United States Patent
Brody et al.

(10) Patent No.: US 8,838,221 B2
(45) Date of Patent: Sep. 16, 2014

(54) AUTOMATIC CATEGORIZATION OF FETAL HEART RATE INFORMATION

(75) Inventors: Gina Brody, Algonquin, IL (US); Caren Busen, Timewell, IL (US); Ning Li, Sequim, WA (US); Randall Paul, Farmington, NM (US); Anne Urmanski, Mableton, GA (US)

(73) Assignee: Clinical Computer Systems Incorporated, Elgin, IL (US)

( * ) Notice: Subject to any disclaimer, the term of this patent is extended or adjusted under 35 U.S.C. 154(b) by 36 days.

(21) Appl. No.: 13/488,112

(22) Filed: Jun. 4, 2012

(65) Prior Publication Data

US 2013/0006132 A1 Jan. 3, 2013

Related U.S. Application Data

(60) Provisional application No. 61/492,688, filed on Jun. 2, 2011.

(51) Int. Cl.
*A61B 5/0444* (2006.01)
*G06F 19/00* (2011.01)
*A61B 5/024* (2006.01)

(52) U.S. Cl.
CPC .......... *G06F 19/3406* (2013.01); *A61B 5/0444* (2013.01); *A61B 5/02405* (2013.01); *A61B 5/02411* (2013.01); *G06F 19/345* (2013.01)
USPC ....................................................... 600/511

(58) Field of Classification Search
CPC ...................................................... A61B 5/0444
USPC ................................................... 600/511, 376
See application file for complete search history.

(56) References Cited

U.S. PATENT DOCUMENTS

| | | | |
|---|---|---|---|
| 5,954,663 A | 9/1999 | Gat | |
| 5,954,666 A | 9/1999 | Snell | |
| 6,306,089 B1 | 10/2001 | Coleman et al. | |
| 6,907,284 B2 | 6/2005 | Hamilton et al. | |
| 8,396,540 B2 | 3/2013 | Miller et al. | |
| 2003/0187364 A1* | 10/2003 | Hamilton et al. | ............. 600/511 |
| 2006/0052704 A1 | 3/2006 | Baba et al. | |
| 2011/0237906 A1* | 9/2011 | Kabakov | ....................... 600/301 |

OTHER PUBLICATIONS

Guijarro-Berdinas, B. et al."An Auto-learning System for the Classification of Fetal Heart Rate Decelerative Patterns," Bio-Inspired Applicaiton of Connectionism, Lecture Notes in Computer Science, 2011, vol. 2085, pp. 393-400 (Abstract Only).

* cited by examiner

*Primary Examiner* — Eric D. Bertram
(74) *Attorney, Agent, or Firm* — Pauley Petersen & Erickson

(57) ABSTRACT

A system and method of documentation and categorization of medical obstetrics data, such as fetal heart rate characteristics. The automatic categorization of fetal heart rate characteristics into three categories, Category I—strongly predictive of normal fetal acid-base balance, Category II—not predictive of abnormal fetal acid-base balance and Category III—predictive of abnormal fetal acid-base balance.

17 Claims, 4 Drawing Sheets

AUTOMATIC CATEGORIZATION OF FETAL HEART RATE INFORMATION

CROSS REFERENCE TO RELATED APPLICATION

This application claims the benefit of U.S. provisional patent application, Ser. No. 61/492,688, filed on 2 Jun. 2011. This provisional patent application is hereby incorporated by reference herein in its entirety and is made a part hereof, including but not limited to those portions which specifically appear hereinafter.

BACKGROUND OF THE INVENTION

1. Field of the Invention

This invention relates generally to a system and a method of electronic documentation and categorization of medical obstetrics data.

2. Discussion of Related Art

In 2008, the National Institute of Child Health and Human Development (NICHD) issued guidelines to provide Labor and Delivery clinicians with unambiguous definitions for the interpretation of fetal heart rate tracings. Fetal heart rates (FHR) are defined by characteristics including baseline FHR, variability, accelerations and decelerations. These combined characteristics allow the fetal heart rate to be classified as Category I (strongly predictive of normal fetal acid-base balance), Category II (indeterminate—not predictive of abnormal fetal acid-base balance, yet there is not enough evidence to classify as Category I or III) or Category III (predictive of abnormal fetal acid-base balance). These, in turn, help clinicians determine appropriate patient management.

Currently, a clinician must evaluate the fetal heart rate tracing, document all required characteristics and then make a determination of the fetal heart rate category, based upon the total of those characteristics. This proves to be a challenge under even optimal conditions, which tend to be rare in today's labor and delivery world. Accordingly, there is a need for a system to automatically categorize medical obstetrics data, such as fetal heart rate patterns.

SUMMARY OF THE INVENTION

The present invention provides a system and method of electronic documentation of medical obstetrics data, such as fetal heart rate monitoring (also known as cardiotocograph monitoring in Europe) and automatic categorization of risk characteristics. The automatic categorization of risk characteristics allows the fetal heart rate to be classified as Category I (strongly predictive of normal fetal acid-base balance), Category II (indeterminate—not predictive of abnormal fetal acid-base balance, yet there is not enough evidence to classify as Category I or III) or Category III (predictive of abnormal fetal acid-base balance). This automatic categorization allows clinicians to determine appropriate patient management quickly and easily and without potential errors of previously known methods.

Although the following description focuses on NICHD documentation guidelines, other standards exist and a similar approach could be taken to appropriately categorize FHR information to these other standards. The present invention includes a fetal heart rate (FHR) categorization tool connected to a data processing unit that processes FHR characteristics into the three categories. The FHR categorization tool may include an interface, such as a graphical user interface (GUI), which allows a clinician to manually enter FHR characteristics into the FHR categorization tool. In a preferred embodiment, the FHR categorization tool is connected to an electronic fetal monitoring system that gathers FHR information. The electronic fetal monitoring system is capable of algorithmically analyzing the FHR information and automatically inputting FHR characteristics into the FHR categorization tool.

In an embodiment of this invention, the GUI includes a window for entering data and displaying results. The window allows the clinician to enter data about the patient such as FHR characteristics. The window may further include a plurality of menus which allow for the selection of a type of FHR categorization; for example but not limited to, fetal heart rate evaluation and fetal heart rate status. The menus may further include a selection to choose FHR categorization based on NICHD documentation guidelines or other standards. The interface further includes a plurality of fields for entry of FHR characteristics such as, baseline FHR, variability, accelerations, decelerations, recurrent (a further classification with respect to decelerations), and sinusoidal. These fields may be manually entered by a clinician and/or automatically populated from data collected and analyzed by the electronic fetal monitoring system. After all required fields are entered, the system activates an add button on the interface and the system calculates and displays a Category I, II or III when the add button is selected. Alternatively, the system may automatically calculate the category upon entering all of the required fields. The category calculation is preferably color-coded to give an additional clear visual indicator as to where the patient falls on the continuum of normal to abnormal. For example, Category I may be color-coded green, Category II may be color-coded yellow and Category III may be color-coded red. However, the categories need not be color-coded or may be color-coded with another set of colors. Other categorization systems (based on standards or protocols other than NICHD standards) may have more than three categories and more than three colors might be used to clearly depict those categories.

This system assists clinicians in NICHD nomenclature-correct documentation of the characteristics of the FHR tracing—baseline, variability, accelerations, and decelerations—through the use of standardized pick-lists. Intelligent documentation prompting will be utilized if additional information about one of the characteristic is necessary, as would be the case for variable or late decelerations with the additional prompting that would occur related to whether or not those are recurrent.

This system also contributes to thoroughness and thoughtfulness of documentation. Categorization of the FHR will preferably not be calculated until the clinician fully documents all of the required characteristics.

This system also provides a "snapshot" view of FHR patterns through a flow sheet including a current evaluation as well as previous evaluations. This allows the clinician to quickly view recent trends over time without having to navigate to another screen. The FHR categorization tool also provides a clear time frame indicator that displays how much time has elapsed between FHR assessments. This includes the date and time of each exam, as well as an automatically calculated interval between each of the posted assessments.

Other advantages will be apparent to those skilled in the art from the following detailed description taken in conjunction with the drawings.

BRIEF DESCRIPTION OF THE DRAWINGS

FIG. 2 is a screen shot showing an initial screen for automatic categorization of fetal heart rate characteristics according to one embodiment of this invention; and FIG. 3 is the screen shot of FIG. 2 with fetal heart rate characteristics entered and a category calculated.

DESCRIPTION OF THE INVENTION

The present invention provides a tool for automatic categorization of fetal heart rate information and methods of use thereof. The device for automatic categorization of fetal heart rate information is preferably useable in connection with Electronic Fetal Monitoring (EFM) systems, such as those EFM systems currently used by and available to medical professionals.

Those skilled in the art and following the teachings herein provided will appreciate that while the descriptions below include preferred configurations, such configurations are used for illustrative purposes only and may be modified as appropriate, depending on need.

The following description of the invention of this application uses the National Institute of Child Health and Human Development's standards for fetal heart rate monitoring and categorization. However, the invention of this application is not limited to this standard and may utilize any standard for categorization of fetal heart rate.

Figure 1:
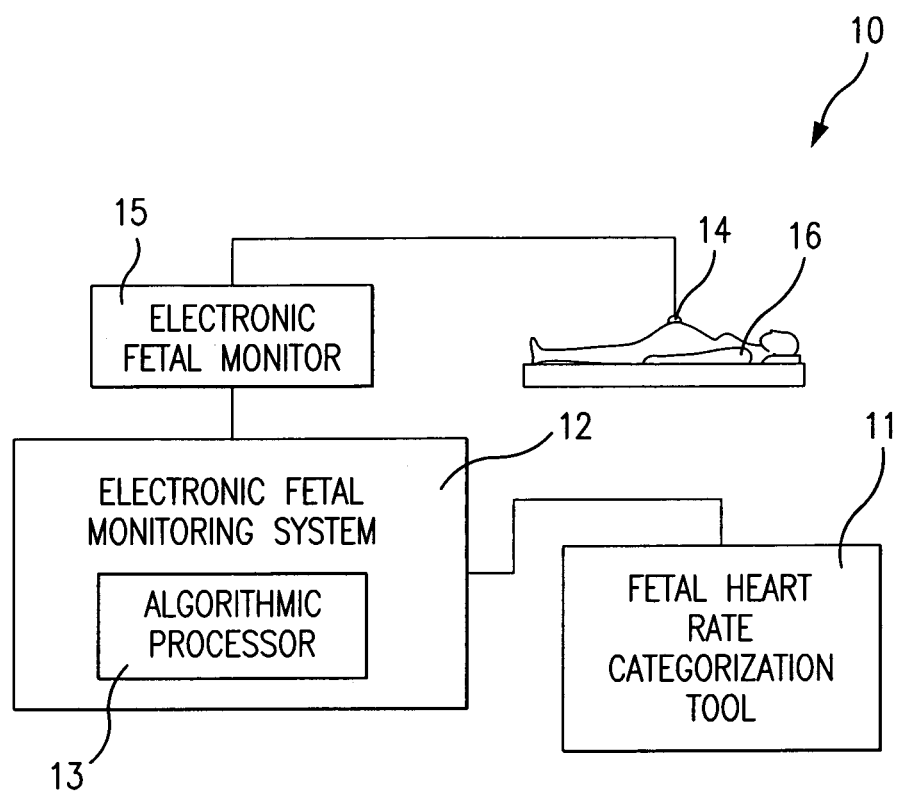
FIG. 1 illustrates an embodiment of the electronic fetal monitoring system of this invention.

FIG. 1 diagrammatically illustrates an embodiment of a categorization system 10 of this invention. In this embodiment, a fetal heart rate (FHR) categorization tool 11 is connected with a representative EFM system 12. In a preferred embodiment, the EFM system 12 of FIG. 1 may include an algorithmic processor 13. The EFM system 12 may also be connected to an electronic fetal monitor 15 which may be connected to a sensor 14 positionable on or about patient 16 for the purpose of gathering fetal heart rate information. Typically, in instances where the measure of fetal heart rate is desired, the sensor(s) 14 are placed upon the abdomen of the patient mother. The sensor 14 can be a single sensor or an array of sensors. The electronic fetal monitor 15 processes the signals from the sensor 14, and the algorithmic processor 13 of the EFM system analyzes the output of the electronic fetal monitor.

Data collected by the sensor 14 is sent to the electronic fetal monitor 15 and/or the EFM system 12. The data processor receives and processes the FHR information to obtain the desired readable output, which is ultimately displayed to a clinician. In one embodiment of this invention, a data processor includes a signal acquisition circuit, a signal analysis circuit, a memory circuit and a display circuit. The term "circuit" as used herein broadly refers to hardware, software, or combination of hardware and software which performs or enables the described function. In one embodiment, the FHR characteristics are collected from at least one of the EFM system 12, the electronic fetal monitor 15 and the sensor 14 and sent to the FHR categorization tool 11 of this invention. In another embodiment of this invention, the FHR categorization tool 11 is only connected to the EFM system 12 and is not connected to the electronic fetal monitor 15 or the sensor(s) 14. In this embodiment, the clinician may read the fetal heart rate characteristics and manually enter this data into the FHR categorization tool 11.

Figure 2:
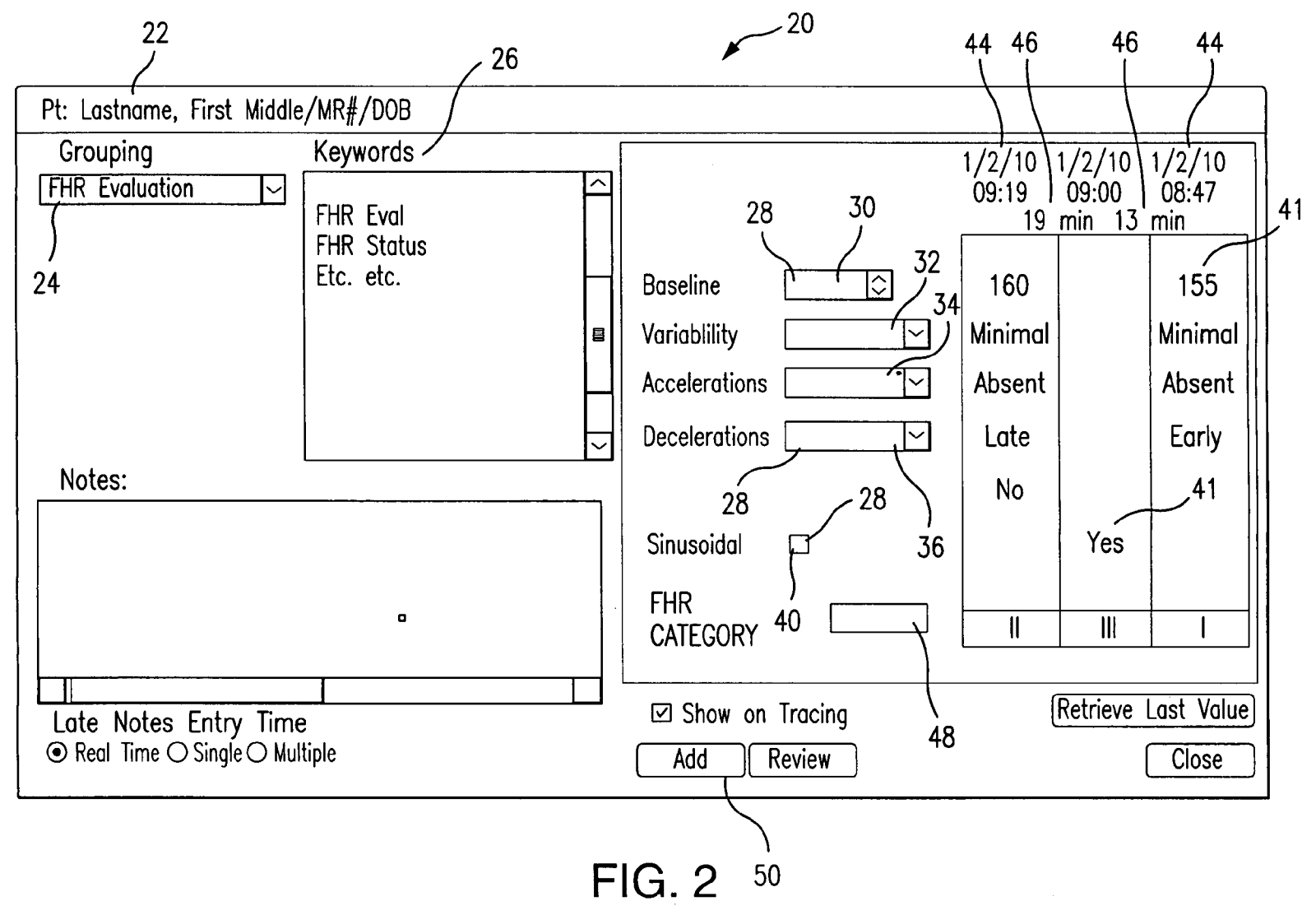
Figure 3:
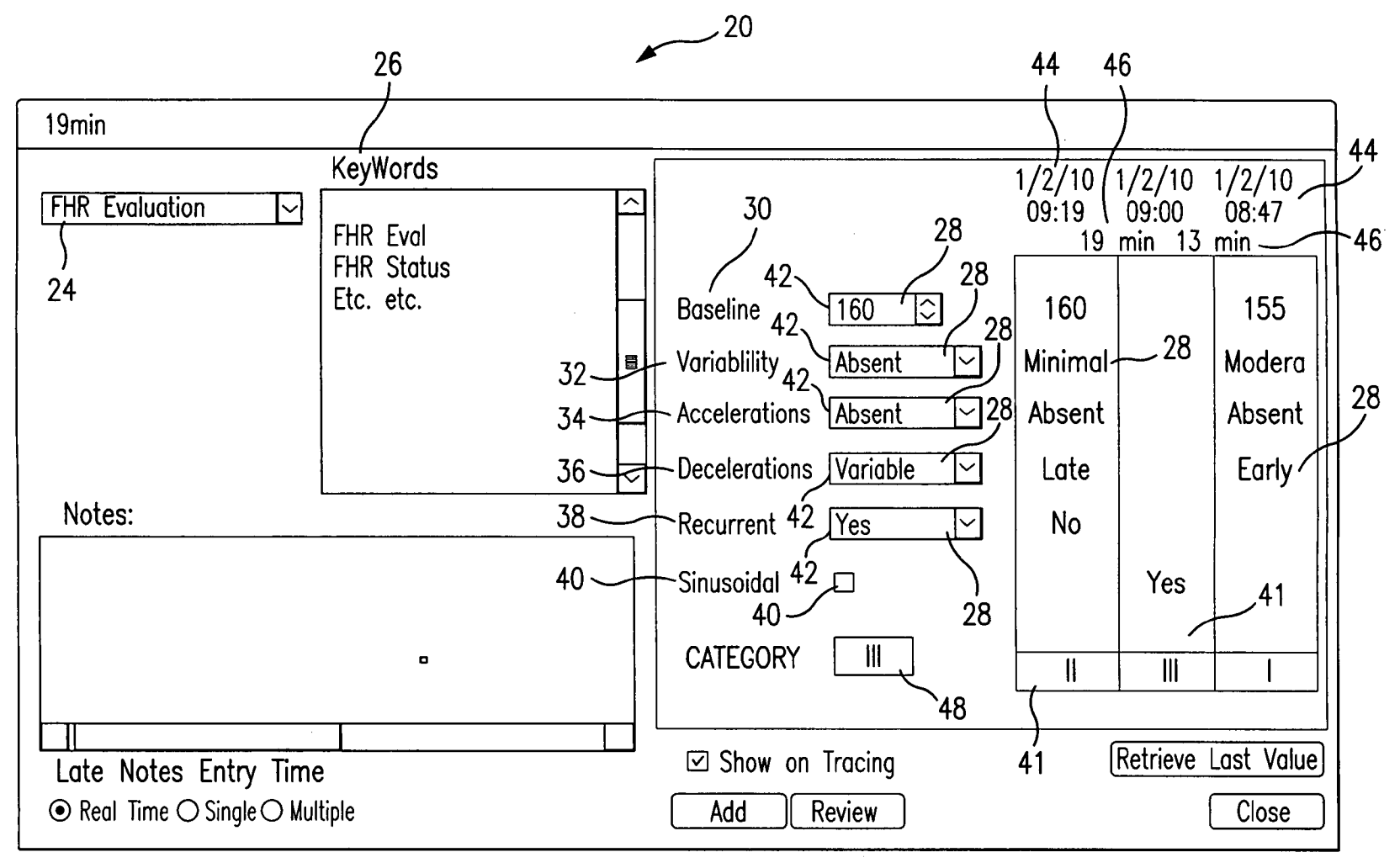

The automatic categorization of FHR is preferably completed in a specialty or niche electronic medical records system within a perinatal clinical area of a hospital. Alternatively, the automatic categorization of FHR is completed in a general or generic electronic medical record (EMR) system used in all or most all the clinical areas including the perinatal area and throughout a healthcare organization. FIGS. 2 and 3 illustrate an exemplary general user interface (GUI) 20 of the FHR categorization tool 11. Initially, as shown in FIG. 2, the GUI 20 includes a plurality of inputs that may be manually entered and/or automatically populated from the data gathered by the EFM system 12, the electronic fetal monitor 15 and the sensor 14, or automatically populated based on data previously entered by the clinician.

At the top of FIG. 2, an identifier 22 is displayed. The identifier 22 creates an association of the FHR categorization to a patient. In this embodiment, the identifier 22 includes entries for last name, first name, middle name, medical record number and date of birth. However, the identifier 22 is not limited to these entries and may include additional entries. The identifier 22 information is provided to the GUI 20 by the Electronic FMS 12 and is not directly entered in the tool.

Preferably, the clinician then selects a grouping 24 from a drop-down menu of FHR Evaluation. Alternatively, the category can be selected in another way including but not limited to manual entry and/or radio buttons. In this embodiment, the grouping 24 is selected as FHR Evaluation.

In a preferred embodiment, upon selection of the grouping 24, a list of keywords 26 may be selected. In the embodiment of FIG. 2, the keywords include, but are not limited to, FHR Eval, and FHR Status.

In a preferred embodiment of this invention, the GUI 20 provides a plurality of inputs 28. As shown in FIGS. 2 and 3, the inputs 28 include a baseline input 30, a variability input 32, an acceleration input 34, a deceleration input 36, a recurrent input 38, and a sinusoidal input 40, however the inputs 28 are not limited to the inputs listed and may include additional inputs. In an alternative embodiment of this invention, the GUI 20 may display different inputs 28 depending on the selected grouping 24, keywords 26 and/or selection of previous inputs 28. In this embodiment, values for each of the baseline input 30, the variability input 32, the acceleration input 34, the deceleration input 36 and the recurrent input 38 are entered using a drop-down menu and the sinusoidal input 40 is selected with a check box. In a preferred embodiment, the drop-down menus allow for the selection of multiple values for each of the inputs. However, the method of selecting each input 28 is not limited to drop-down menus and check boxes and may comprises any input device, including but not limited to, slider bars, type-in entry boxes and radio buttons. In an alternative embodiment, one or more of the baseline input 30, the variability input 32, the acceleration input 34, the deceleration input 36, the recurrent input 38 and the sinusoidal input 40 may be automatically populated from data algorithmically analyzed and collected by the EFM system 12, the sensor 14 and/or previously entered inputs 28. Table 1 shows a preferred embodiment of the possible inputs to the baseline input 30, the variability input 32, the acceleration input 34, the deceleration input 36, the recurrent input 38 and the sinusoidal input 40.

TABLE 1

| DATA POINT | OPTIONS | COMMENTS |
|---|---|---|
| Baseline | Numerical; any increment of 5 bpm between 30 and 240 bpm | Numerical value list (30-240, increments of 5) |
| Variability | Absent<br>Minimal | Multi-select checklist<br>Only 1 can be checked |

TABLE 1-continued

| DATA POINT | OPTIONS | COMMENTS |
|---|---|---|
| | Moderate | |
| | Marked | |
| | Cannot Determine | |
| Accelerations | Present | Multi-select checklist |
| | Absent | Only 1 can be checked |
| | Cannot Determine | |
| Decelerations | Absent | Multi-select checklist |
| | Early | Check ALL that apply |
| | Variable | If ABSENT is checked and |
| | Late | the user selects another |
| | Prolonged | answer, an error message |
| | Cannot Determine | should be displayed |
| Recurrent | Present | Multi-select checklist |
| Decelerations | Absent | Only 1 can be checked |
| | Cannot Determine | Should only present to user if Early, Variable, Late or Prolonged decelerations are checked |
| Sinusoidal Pattern | Absent | Check-box; Check in Box = Present, No Check in Box = Absent |
| | Present (for at least 20 minutes) | |

Baseline refers to baseline fetal heart rate (baseline FHR). The National Institute of Child Health and Human Development (NICHD) defines baseline FHR as the mean FHR rounded to increments of 5 beats per minute (bpm) during a 10 minute window, excluding accelerations and decelerations and periods of marked FHR variability (greater than 25 bpm). There must be at least 2 minutes of identifiable baseline segments (not necessarily contiguous) in any 10 minute window or the baseline for that period is indeterminate. The normal baseline FHR range is typically between about 110 and about 160 bpm. Fetal bradycardia is generally determined if the baseline FHR is below 110 bpm, and fetal tachycardia is generally determined if the baseline FHR is above 160 bpm.

The NICHD nomenclature defines variability as fluctuations in the baseline FHR that are irregular in amplitude and frequency. The fluctuations are visually quantitated as the amplitude of the peak-to-trough in beats per minute (bpm). The variability is categorized by the quantitated amplitude as: (1) absent—undetectable;. (2) minimal—greater than undetectable, but less than or equal to 5 bpm; (3) moderate—greater than or equal to 6 bpm and less than or equal to 25 bpm; and (4) marked—greater than 25 bpm. Baseline FHR variability is determined in a 10 minute window, excluding accelerations and decelerations.

NICHD defines acceleration as a visually apparent abrupt increase in FHR. An abrupt increase is defined as an increase from the onset of acceleration to peak in less than or equal to 30 seconds. To be called an acceleration, the peak must be greater than or equal to 15 bpm, and the acceleration must last greater than or equal to 15 seconds from the onset to return. A prolonged acceleration is greater than or equal to 2 minutes but less than 10 minutes in duration. An acceleration lasting greater than or equal to 10 minutes is defined as a baseline change. Before 32 weeks of gestation, acceleration are defined as having a peak greater than or equal to 10 bpm and a duration of greater than or equal to 10 seconds.

NICHD Identifies Four Types of Deceleration:
1. Early deceleration: Visually apparent, usually symmetrical, gradual decrease and return of the FHR associated with a uterine contraction. A gradual FHR decrease is defined as one from the onset to the FHR nadir of greater than or equal to 30 seconds. The decrease in FHR is calculated from the onset to the nadir of the deceleration. The nadir of the deceleration occurs at the same time as the peak of the contraction. In most cases the onset, nadir, and recovery of the deceleration are coincident with the beginning, peak, and ending of the contraction, respectively.
2. Late deceleration: Visually apparent usually symmetrical gradual decrease and return of the FHR associated with a uterine contraction. A gradual FHR decrease is defined as from the onset to the FHR nadir of greater than or equal to 30 seconds. The decrease in FHR is calculated from the onset to the nadir of the deceleration. The deceleration is delayed in timing, with the nadir of the deceleration occurring after the peak of the contraction. In most cases, the onset, nadir, and recovery of the deceleration occur after the beginning, peak, and ending of the contraction, respectively.
3. Variable deceleration: Visually apparent abrupt decrease in FHR. An abrupt FHR decrease is defined as from the onset of the deceleration to the beginning of the FHR nadir of less than 30 seconds. The decrease in FHR is calculated from the onset to the nadir of the deceleration. The decrease in FHR is greater than or equal to 15 beats per minute, lasting greater than or equal to 15 seconds, and less than 2 minutes in duration. When variable decelerations are associated with uterine contractions, their onset, depth, and duration commonly vary with successive uterine contractions.
4. Prolonged deceleration: A prolonged deceleration is present when there is a visually apparent decrease in FHR from the baseline that is greater than or equal to 15 bpm, lasting greater than or equal to 2 minutes, but less than 10 minutes. A deceleration that lasts greater than or equal to 10 minutes is a baseline change.

Additionally, decelerations can be recurrent or intermittent based on their frequency (more or less than 50% of the time) within a 20 minute window.

NICHD guidelines define a sinusoidal heart rate as a pattern of regular variability resembling a sine wave, with fixed periodicity of 3-5 cycles per minute and amplitude of 5-40 beats per minute. Sinusoidal patterns are categorized as Category III tracings and may indicate fetal anemia caused by fetomaternal hemorrhage or alloimmunization. If a clinician checks the sinusoidal input 40, the tracing is automatically considered to be Category III tracing. In a preferred embodiment of this invention, checking the sinusoidal input 40 box causes at least one of the other input fields to be grayed-out, preventing entry of a value.

In a preferred embodiment of this invention, the GUI 20 includes columns 41 listing values 42 of the inputs 28 for a plurality of previous exams. The columns 41 are preferably resizable to accommodate the length of inputs 28. The GUI 20 also preferably includes a date and time stamp 44 for each of the plurality of exams at a top of the column and an interval 46 of time elapsed between each of the plurality of exams. In a preferred embodiment, at least one of the date and time stamp 44 and the interval 46 may be stored and/or sent to flowsheet.

In a preferred method of operation, the clinician enters the identifier 22 information into the FHR categorization tool 11 and selects at least one of the grouping 24 and the keyword 26. The clinician then enters values for the baseline input 30, the variability input 32, the acceleration input 34 and/or the deceleration input 36. In a preferred embodiment, if the deceleration input 36 is entered with variable deceleration or late deceleration, a selection box (yes or no) displays for the recurrent input 38. Alternatively, the recurrent input 38 is displayed regardless of an entry to the deceleration input 36. In a preferred embodiment, the clinician must either enter an entry into all of the baseline input 30, the variability input 32, the acceleration input 34 and the deceleration input 36 (with the recurrent input 38, if applicable) or select the sinusoidal input 40 in order for the FHR category 48 to be calculated and displayed. In one embodiment, entering in values for each the inputs 30, 32, 34, 36, 38 or the sinusoidal input 40 causes the FHR categorization tool 11 to automatically calculate the FHR category 48. In an alternative embodiment, the entering in values for each the inputs 30, 32, 34, 36, 38 or the sinusoidal input 40 activates an add button 50 that must be selected to calculate the FHR category 48. In another embodiment of this invention, the FHR category 48 calculation is dynamic, meaning that the FHR category 48 is calculated as the clinician is entering information.

Figure 4:
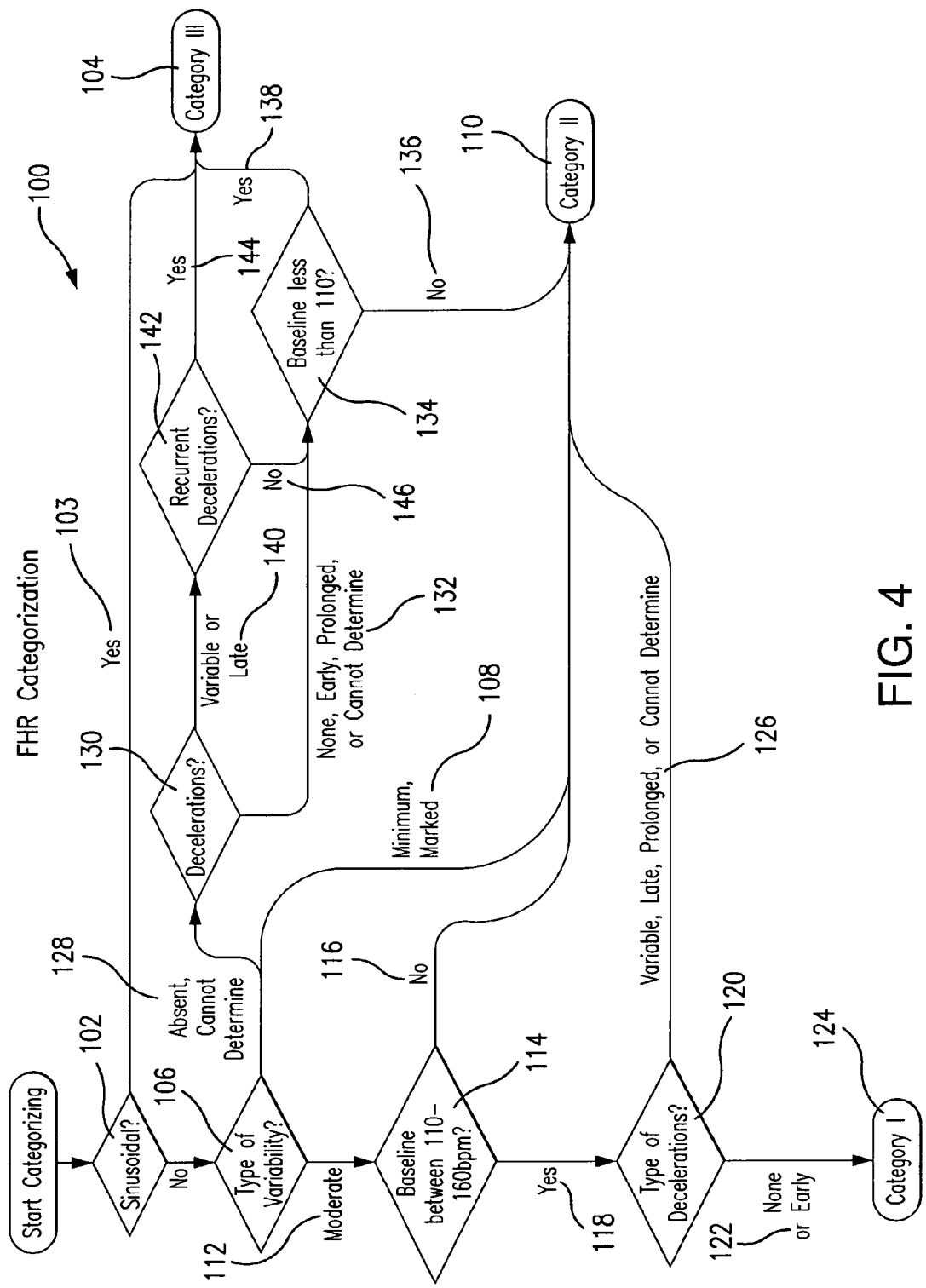
FIG. 4 is a flow chart for a method of calculating categories according to one embodiment of this invention and based on NICHD standards.

FIG. 4 shows a flowchart 100 for FHR categorization according to one embodiment of this invention. In this embodiment, the categorization process begins by evaluating whether the FHR is sinusoidal 102. If the FHR is sinusoidal 103, the FHR is categorized as Category III 104, a FHR Category output 48 on the GUI 20 displays "III" in a red box indicating that the clinician should take appropriate steps to monitor and treat the patient.

If the categorization process determines that the FHR is not sinusoidal, the process checks for a type of variability 106—absent, minimum, moderate, marked or cannot determine.

If the variability is minimum or marked 108, the FHR is categorized as Category II 110, the FHR Category output 48 on the GUI 20 displays "II" in a yellow box indicating that the clinician should take a cautious approach with the patient.

If the variability is moderate 112, the baseline FHR is evaluated to determine if it is between 110-160 bpm. If the baseline FHR is not between 110-160 bpm 116, the FHR is categorized as Category II 110 and the FHR Category output 48 on the GUI 20 displays "II" in a yellow box indicating that the clinician should take a cautious approach with the patient. If the baseline FHR is between 110-160 bpm 118, the FHR categorization process 100 checks for a type of deceleration 120—none, early, variable, late, prolonged, or cannot determine. If the deceleration is none or early 122, the FHR is categorized as Category I 124 and the FHR Category output 48 on the GUI 20 displays "I" in a green box indicating that the clinician should take a standard approach with the patient. If the deceleration is variable, late prolonged or cannot determine 126, the FHR is categorized as Category II 110 and the FHR Category output 48 on the GUI 20 displays "II" in a yellow box indicating that the clinician should take a cautious approach with the patient.

If the variability is absent or cannot determine 128, the FHR categorization process 100 checks for a type of deceleration 130—none, early, variable, late, prolonged, or cannot determine. If the decelerations are none, early, prolonged or cannot be determined 132, then check if the baseline FHR is greater than or less than 110 bpm 134. If the baseline FHR is less than 110 bpm 136, the FHR is categorized as. Category II 110 and the FHR Category output 48 on the GUI 20 displays "II" in a yellow box indicating that the clinician should take a cautious approach with the patient. If the baseline FHR is greater than or equal to 110 bpm 138, then the FHR is categorized as Category III 104, the FHR Category output 48 on the GUI 20 displays "III" in a red box indicating that the clinician should take appropriate steps to monitor and treat the patient. If the decelerations 130 are variable or late 140, then check for recurrent decelerations 142. If there are recurrent decelerations 144, then the FHR is categorized as Category III 104, the FHR Category output 48 on the GUI 20 displays "III" in a red box indicating that the clinician should take appropriate steps to monitor and treat the patient. If there are no recurrent decelerations 146, then check if the baseline FHR is greater than or less than 110 bpm 134. If the baseline FHR is less than 110 bpm 136, the FHR is categorized as Category II 110 and the FHR Category output 48 on the GUI 20 displays "II" in a yellow box indicating that the clinician should take a cautious approach with the patient. If the baseline FHR is greater than or equal to 110 bpm 138, then the FHR is categorized as Category III 104, the FHR Category output 48 on the GUI 20 displays "III" in a red box indicating that the clinician should take appropriate steps to monitor and treat the patient.

The invention illustratively disclosed herein suitably may be practiced in the absence of any element, part, step, component, or ingredient, which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. An apparatus for documentation and categorization of fetal heart rate comprising:
an Electronic Fetal Monitoring system to analyze fetal heart rate characteristics;
an interface for entering values for a plurality of inputs of fetal heart rate characteristics, wherein the plurality of inputs include at least one of a baseline input, a variability input, an acceleration input, a deceleration input and a sinusoidal input, and wherein selection of the sinusoidal input prevents entry of an input to at least one of the baseline input, the variability input, the acceleration input and the deceleration input;
a data processor in combination with the interface to receive and process the plurality of fetal heart rate characteristics; and
wherein the interface displays a category alert from a plurality of possible categories depending on a calculation of the plurality of inputs of fetal heart rate characteristics.

2. The apparatus for documentation and categorization of fetal heart rate of claim 1, wherein the plurality of possible categories comprises a Category I, a Category II and a Category III.

3. The apparatus for documentation and categorization of fetal heart rate of claim 2, wherein the category alert is color-coded.

4. The apparatus for documentation and categorization of fetal heart rate of claim 1, wherein the plurality of inputs further includes a recurrent input.

5. The apparatus for documentation and categorization of fetal heart rate of claim 1, wherein the interface will not display the calculated category unless each of the baseline input, the variability input, the acceleration input and the deceleration input receive entries or until the sinusoidal input is selected.

6. The apparatus for documentation and categorization of fetal heart rate of claim 1, wherein the plurality of categories comprise a National Institute of Child Health and Human Development issued standards for interpretation of fetal heart tracings.

7. The apparatus for documentation and categorization of fetal heart rate of claim 1, further including:
at least one sensor positionable on or about a patient to measure fetal heart rate information.

8. The apparatus for documentation and categorization of fetal heart rate of claim 1, wherein the interface displays a plurality of columns showing an input history of the values for the plurality of inputs of fetal heart rate characteristics and a calculation history of the categories.

9. The apparatus for documentation and categorization of fetal heart rate of claim 8, wherein the interface displays an interval between at least two of the input histories.

10. An apparatus for documentation and categorization of fetal heart rate comprising:
  an Electronic Fetal Monitoring system to analyze fetal heart rate characteristics;
  an interface for entering values for a plurality of inputs of fetal heart rate characteristics;
  a data processor in combination with the interface to receive and process the plurality of fetal heart rate characteristics;
  wherein the interface displays a category alert from a plurality of possible categories depending on a calculation of the plurality of inputs of fetal heart rate characteristics; and
  wherein a method of categorization of fetal heart rate via the apparatus of comprises:
    positioning a sensor in proximity to a patient to measure a fetal heart rate information;
    inputting values for the plurality of inputs of the fetal heart rate characteristics;
    calculating the category from the inputs of the fetal heart rate characteristics; and
    displaying the category on interface, wherein the category comprises a Category I, a Category II and a Category III corresponding to National Institute of Child Health and Human Development guidelines.

11. The method of categorization of fetal heart rate of claim 10, wherein at least one of the fetal heart rate information and the fetal heart rate characteristics include at least one of a baseline FHR, a variability FHR, an acceleration FHR, a deceleration FHR and a sinusoidal FHR.

12. The method of categorization of fetal heart rate of claim 11, wherein:
  the baseline FHR comprises a mean FHR;
  the variability FHR comprises one of an absent variability, a minimum variability, a moderate variability, a marked variability and a cannot determine variability;
  the deceleration FHR comprises one of an absent deceleration, an early deceleration, a late deceleration, a variable deceleration, a prolonged deceleration and a cannot determine deceleration;
  and the sinusoidal FHR comprises one of yes or no.

13. The method of categorization of fetal heart rate of claim 12, wherein if the FHR deceleration equals one of the variable deceleration and the late deceleration, the fetal heart rate characteristics further include a presence of a recurrent deceleration.

14. The method of categorization of fetal heart rate of claim 13, wherein selecting yes for the sinusoidal FHR results in the Category III being displayed.

15. The method of categorization of fetal heart rate of claim 10, wherein displaying the category further includes a color code.

16. The method of categorization of fetal heart rate of claim 10, wherein the interface includes a previously calculated category and previous values for the plurality of inputs.

17. The method of categorization of fetal heart rate of claim 16, wherein the interface further includes an interval of time from the previously calculated category.

* * * * *